United States Patent [19]

Smith et al.

[11] Patent Number: 5,599,983
[45] Date of Patent: Feb. 4, 1997

[54] PREPARATION OF ALKANESULFONAMIDES WITH LOW RESIDUAL AMMONIUM IMPURITIES

[76] Inventors: Gary S. Smith, 7 Cardinal La., Collegeville, Pa. 19426; Robert Cordova, 1053 Blake St., Bethlehem, Pa. 18017; Thomas H. Overgaard, 18263 Denby, Redford Township, Mich. 48246; Marc T. Budrick, 15298 Regina, Allen Park, Mich. 48101

[21] Appl. No.: 517,320

[22] Filed: Aug. 21, 1995

[51] Int. Cl.$^6$ ............................................ C07E 303/44
[52] U.S. Cl. ............................................................ 564/98
[58] Field of Search ...................................... 564/98

[56] References Cited

U.S. PATENT DOCUMENTS

| | | | |
|---|---|---|---|
| 3,574,740 | 4/1971 | Martin | 260/556 |
| 4,970,339 | 11/1990 | Sandler et al. | 564/98 |
| 5,068,427 | 11/1991 | Sandler et al. | 564/84 |
| 5,159,112 | 10/1992 | Ollivier et al. | 564/98 |
| 5,166,431 | 11/1992 | Sandler et al. | 564/98 |

FOREIGN PATENT DOCUMENTS

0504873A1  9/1992  European Pat. Off. .

OTHER PUBLICATIONS

Field and Grunwald, "Symmetrical 1,3–Bis–(alkane–and arylsulfonyl)–Ureas", J. Amer. Soc., vol. 75, pp. 934–937 (1953).

*Primary Examiner*—Peter O'Sullivan

[57] ABSTRACT

A method is disclosed for the preparation of alkanesulfonamide containing low amounts of ammonium or alkylammonium-salt impurities wherein alkanesulfonamide is treated with a base to convert ammonium or alkylammonium-salt impurities to their corresponding base salts and to liberate neutral amine or ammonia.

26 Claims, No Drawings

PREPARATION OF ALKANESULFONAMIDES WITH LOW RESIDUAL AMMONIUM IMPURITIES

BACKGROUND OF THE INVENTION

This invention relates to the preparation of low ammonium or alkylammonium salts of alkanesulfonamides and their analogues. More particularly, it relates to a method for converting substantially all of the ammonium or alkylammonium salt impurities of an alkanesulfonamide to the corresponding alkali-metal or alkaline-earth metal salts.

In the preparation of alkanesulfonamides, or otherwise, the alkanesulfonamides may become contaminated with the ammonium or amine salts of the reaction by-products. Due to their incorporation in reaction amines, these salts may cause the formation of other unwanted by-products when the contaminated sulfonamide is employed in certain syntheses. This invention provides a method of reducing the ammonium or alkylammonium ion content of the contaminated sulfonamide by replacement of the ammonium or alkylammonium ions with alkali-metal or alkaline-earth metal ions. After such a treatment, the alkanesulfonamide may then be included in various subsequent synthetic reactions without the formation of unwanted by-products.

THE PRIOR ART

Preparation of alkanesulfonamides from the corresponding alkanesulfonyl halides (chlorides), with formation of ammonium halide by-product is well known in the art. In European Patent 0,504,873 of Sep. 23, 1992, alkanesulfonamides are prepared from the reaction of alkanesulfonyl chloride with $\leq 2$ molar equivalents of a reactive amine in a halogenated aromatic solvent, followed by treatment of the reaction mixture with aqueous alkali-metal hydroxide to convert the amine hydrochloride by-product to alkali-metal chloride and to liberate amine. In U.S. Pat. No. 5,068,427 of November, 1991, there is disclosed the treatment of a crude alkanesulfonamide containing $NH_4Cl$ and a small amount of ammonium alkanesulfonimide, with an aqueous alkali-metal hydroxide to form alkali-metal chloride, water and ammonia.

These prior teachings fail to disclose or suggest the replacement of the ammonium ions of the salts of alkanesulfonate or alkanesulfonimide with alkali-metal or alkaline-earth metal ions by either aqueous or anhydrous means.

Alkali-metal and alkaline-earth metal salts of alkanesulfonamides are also known, e.g., in Jour. Amer. Chem. Soc., Vol. 75, p. 934 (1953). However, the use of these alkanesulfonamide salts as bases for the conversion of ammonium halides, alkanesulfonates, and alkanesulfonimides to their respective metal salts has not been suggested.

STATEMENT OF THE INVENTION

This invention is a method for the preparation of an alkanesulfonamide containing reduced amounts of ammonium or alkylammonium ion impurities comprising the treatment of an alkanesulfonamide containing ammonium or alkyl ammonium salts with a base under substantially anhydrous conditions and in an amount sufficient to convert substantially all of said salts to their corresponding base salt, and liberating neutral amine or ammonia from the reaction, said base selected from the group consisting of alkali-metal and alkaline-earth metal bases, quaternary ammonium and phosphonium bases, and synthetic polymeric resins containing basic functionalities.

DETAILED DESCRIPTION OF THE INVENTION

This invention is a method for preparing alkanesulfonamides and related products having a low ammonium or alkylammonium-ion content by the replacement of said ions in their salts with alkali-metal or alkaline-earth metal ions. Preferably, the alkanesulfonamides have the formula

$$RSO_2NR^1R^2$$

where R is a $C_1$–$C_{20}$ alkyl, and $R^1$ and $R^2$ are independently hydrogen or $C_1$–$C_{20}$ alkyl. More preferably, R is methyl or ethyl and $R^1$ and $R^2$ are the same or different and independently selected from hydrogen or methyl. Most preferably, the alkanesulfonamide is methanesulfonamide.

Synthetic methods for the preparation of alkanesulfonamides are well known and include, for example, the treatment of the corresponding alkanesulfonyl halide with a reactive amine, e.g., ammonia or a primary or secondary amine, in the presence of various volatile organic solvents with subsequent removal of the bulk of the ammonium or alkylammonium halide by-product. The synthesis provides a crude product which is predominantly alkanesulfonamide but also contains minor amounts of the ammonium or alkylammonium alkanesulfonate, alkanesulfonimide, and halide. (Hereinafter "ammonium" will be used to refer to both ammonium and alkylammonium ions).

When alkanesulfonamides contaminated with ammonium salts are employed in reactions with other chemical species such that the sulfonamide nitrogen becomes further substituted, the ammonium salt impurities may act as sources of ammonia or amines and lead to the competitive formation of undesirable by-products. Examples of reactions of alkanesulfonamides where the presence of the ammonium salt impurities would be deleterious include those reactions with organohalide or anhydride substrates, especially when the reactions are performed under alkaline conditions. Depending on the nature of the substrate, the undesirable by-products would be the amines, amides, and imides derived from the ammonium impurities and the substrate.

In this invention, alkanesulfonamide products containing ammonium-salt impurities are treated with a base, under substantially anhydrous conditions, with the removal of the liberated $NH_3$ or amine by conventional means. This procedure has the advantage of providing an alkanesulfonamide product wherein the ammonium-salt impurities have been substantially eliminated and replaced with metal salt analogues of the impurities which will not substantially interfere with the subsequent reactions of the alkanesulfonamide described above. The base-treated alkanesulfonamides contain only residual traces of $NH_3$ or amine-producing impurities, and are more suitable and thus superior to the original untreated alkanesulfonamides for use in certain applications.

Advantages of the process of the invention are that it permits the use of a controlled amount of base in the absence, or substantial absence, of water. The need to neutralize the entire amount of amine hydrochloride remaining after the manufacture of the alkanesulfonamide is alleviated as well as the requirement of distilling off significant volumes of water. Difficult to separate solvent-water mixtures are also avoided. Furthermore, the process does not suffer from the need to dispose of large amounts of alkanesulfonamide—contaminated metal halide.

The alkanesulfonamides, particularly methanesulfonamide, have commercial utility such as in the manufacture of herbicidal compounds, for example, see U.S. Pat. No. 4,285,723.

In accordance with this invention, crude alkanesulfonamides containing ammonium impurities are treated with an alkali-metal or alkaline-earth metal base (or other defined base) to convert the impurities to their corresponding salts. Such a treatment liberates the amine portion of the impurity and permits its removal by conventional means such as distillation, entrainment in an inert gas, co-distillation with a solvent, or solvent extraction.

Ammonium-salt impurities in the crude which are effected by the base treatment include the ammonium halides, alkanesulfonates, and alkanesulfonimides. These salts often have enough inherent solubility in the reaction medium that they cannot be completely removed by simple methods. Thus, they will remain as impurities in the alkanesulfonamide product after removal of the solvent.

As previously discussed, the crude alkanesulfonamides which may be employed as starting materials in this invention are typically synthesized by the reaction of an alkanesulfonyl halide (chloride) and a reactive amine, with the reaction being performed in an organic solvent whose properties include a high solubility for the alkanesulfonamide product and a poor solubility for the amine hydrochloride by-product. Typical volatile organic solvents include, for example, at least one of acetonitrile, 1,2-dimethoxyethane, diethoxymethane, 1,3-dioxolane, 1,4-dioxane, a $C_1$–$C_4$ nitroalkane, propionitrile, tetrahydrofuran or toluene. When the reaction is performed in such a solvent, the bulk of the amine hydrochloride by-product can be separated from the final reaction mixture by filtration, centrifugation or decantation. The alkanesulfonamide product can then be recovered by removal of the solvent. An example of such a process is the manufacture of methanesulfonamide and ammonium chloride in tetrahydrofuran solvent from methanesulfonyl chloride and anhydrous ammonia gas.

Since it would be desirable that the alkanesulfonamide product be of high purity after the base treatment, the use of the minimal amount of base required to achieve the neutralization of the ammonium impurities would be advantageous. Thus, it is preferred to remove the bulk of the amine hydrochloride by-product from the alkanesulfonamide-synthesis mixture by filtration and to base-treat the resulting filtrate. In this manner, the treatment with base to neutralize the ammonium salt impurities can then be performed in the synthesis solvent, followed by simultaneous removal of the liberated amine and the solvent by distillation or other conventional means. Alternatively, the solvent can be removed first and the base added directly to the resulting alkanesulfonamide at such a temperature that the alkanesulfonamide is above its melting point. The liberated amine thus produced is then removed from the treated alkanesulfonamide product, and recovered for future use, by any of several methods including distillation, entrainment in an inert gas stream or decantation.

The salts derived from the neutralization of the ammonium impurities may remain in the alkanesulfonamide product as impurities; however, these materials are usually either innocuous or are not present in sufficient concentrations to be deleterious in subsequent reactions employing the alkanesulfonamide. In certain cases, the salts obtained after the base treatment are insoluble in the alkanesulfonamide/solvent mixture. In these situations, it is possible to remove the salts from the mixture by filtration. This latter variation can afford an alkanesulfonamide product containing both low levels of ammonium impurities and reduced levels of other salt impurities. An example of such a case is the KOH-neutralization of ammonium methanesulfonate, ammonium chloride, and ammonium methanesulfonamide impurities in a methanesulfonamide/tetrahydrofuran matrix.

Any one of the known alkali-metal or alkaline-earth metal inorganic bases can be used for the neutralization of the ammonium impurities in the alkanesulfonamides. The only absolute criteria governing the selection of the base are that it be of sufficient strength to effect the neutralization, and that it be sufficiently soluble in either the alkanesulfonamide/solvent mixture or in the neat liquid alkanesulfonamide such that efficient contact with ammonium impurities can be realized. Examples of alkali-metal or alkaline-earth metal bases suitable for use in this invention include the commercially-available hydroxides, carbonates, bicarbonates, oxides, phosphates and pyrophosphates of sodium, potassium, calcium and magnesium. If desired, the bases may be mounted on an inert solid carrier.

Other criteria which are required are that the base should be anhydrous or essentially anhydrous and that it should not generate any appreciable water as part of the neutralization reaction. These latter criteria become particularly important when the base-treatment occurs in water-miscible solvents such as tetrahydrofuran. In these cases, the presence of water in the solvent after recovery can limit its recyclability in the process, or require the use of expensive solvent drying procedures. In this situation, the least preferred, but still useful, alkaline bases would be the hydroxides and bicarbonates.

The selection of the alkali or alkaline earth metal component of the base is governed by (i) particular preferences related to the ultimate application of the treated alkanesulfonamide product, and (ii) the desire to minimize any negative impact on the purity of the treated alkanesulfonamide arising from the introduction of the metal. When the latter is of overriding importance, the alkaline-earth metal bases would be preferred over the alkali-metal bases.

Quaternary ammonium and phosphonium hydroxides, carbonates, phosphates, and pyrophosphates, as well as synthetic polymeric resins, e.g., ion-exchange resins, containing these functionalities, are known analogues to the alkali-metal bases employed in this invention, and thus are also suitable for use in this process. These bases will include, for example, the $C_4$–$C_{32}$ tetra(alkyl) or tetra(arylalkyl) ammonium or phosphonium bases.

The amount of alkaline base to be employed in the neutralization of the ammonium impurities is governed by the amounts of the impurities present in the crude alkanesulfonamide or alkanesulfonamide/solvent mixture. The levels of the ammonium halide, ammonium alkanesulfonates, and ammonium alkanesulfonimide present can be determined by any one of several means, such as high performance liquid chromatography (suppressed or non-suppressed), ion chromatography, capillary electrophoresis, or titrimetric analyses. Based on the amount of ammonium present in the crude alkanesulfonamide and the stoichiometry associated with the neutralization by a given alkaline base, an amount of base can be charged such that all of the ammonium is neutralized, or that the ammonium concentration is reduced to a target level. In that the amount of ammonium salt impurities in the alkanesulfonamides are relatively low (generally <2%), a slight overcharge of the base is not particularly deleterious to the overall assay. However, a significant overcharge of base may lead to the reaction of the alkanesulfonamide with the base, resulting in decreases in the perceived purity of the treated product.

The propensity of the alkanesulfonamides of the formula $RSO_2NR^1H$, where R and $R^1$ are both $C_1$–$C_{20}$ alkyl to react with alkali metal or alkaline earth metal bases as disclosed, for example, in the Jour. Amer. Chem. Soc., Vol. 75, p. 934 (supra) can, in fact, be put to advantageous use. These metal alkanesulfonamide salts can be especially well suited for use as alternative bases in this invention. Relative to the ammonium halide, alkanesulfonate and alkanesulfonimide impurities in the crude alkanesulfonamide, the metal alkanesulfonamides are relative strong bases. Moreover, the neutralization of the ammonium impurities with a metal alkanesulfonamide returns the neutral alkanesulfonamide as one of the products. Metal alkanesulfonamides would be prepared by established methods, such as reacting the alkanesulfonamide with a stoichiometric amount of alkali- or alkaline-earth metal hydroxide or alkoxide, followed by distillative removal of either water or alkanol. In accordance with this invention, an appropriate portion of the prepared metal alkanesulfonamide would be used as the base to neutralize the ammonium salt impurities in crude alkanesulfonamides.

The temperature range within which the base treating method of this invention is conducted is generally from about 10° to about 130° C., preferably from 40° to 110° C. These temperatures apply to both the neutralization procedure and to the amine and solvent-stripping step. The pressure used during the solvent and amine-stripping step ranges from about 1 to 760 mm Hg, preferably from about 40 to about 760 mm Hg.

The preferred mole ratio of the reaction of inorganic base, as hydroxides or bicarbonates, with each mole of ammonium ion is generally from about 0.25 to 1.2 while the carbonate, oxide and pyrophosphate bases have a preferred mole ratio range from about 0.1 to 1.2 per mole of ammonium ion. The metal (alkali or alkaline-earth) alkanesulfonamides are used in a mole ratio of from about 0.25 to 1.2 for each mole of ammonium ion. The base functional synthetic resins and the quaternary ammonium and phosphonium bases will be useful in the mole ratio range of 0.1 to 1.5 base equivalents for each mole of ammonium ion. The mole ratios given are moles of base for each mole of ammonium ion in the crude starting sulfonamide or in the crude sulfonamide/solvent mixture.

The base treating process of this invention may be operated using batch or continuous procedures, as preferred. In some situations, it has been found advantageous to employ a packed column or static bed of the base, preferably the phosphates and pyrophosphates, to continuously treat the ammonium salt impurities in a crude alkanesulfonamide product passing therethrough. The phosphates and pyrophosphates are preferred for treatment in the column or bed procedures because of their abilities to be formed into hard pellets, briquettes, crystals and the like shapes.

The following examples are set forth to demonstrate this invention:

EXAMPLE 1

Crude methanesulfonamide was obtained from the reaction of methanesulfonyl chloride and ammonia in tetrahydrofuran, with removal of most of the ammonium chloride by-product by centrifugation, and distillative removal of the tetrahydrofuran solvent. A portion of this crude methanesulfonamide (34 g.) containing 0.64% ammonium methanesulfonate, 0.15% ammonium methanesulfonimide, and 0.18% ammonium chloride, was dissolved in tetrahydrofuran (166 g.) and the resulting solution heated to 60° C. Anhydrous potassium carbonate (0.502 g.) was added and the mixture allowed to stir for 15 minutes. The evolution of a gas was observed at the time of the addition of the base. The cloudy mixture was then stripped on a rotary evaporator at reduced pressure to remove the tetrahydrofuran solvent, and the resulting solid product allowed to dry overnight at 80° C. Analyses of the dried methanesulfonamide product derived from this treatment revealed an $NH_4^+$ (ammonium ion) concentration of 115 ppm, as compared to 1750 ppm in the crude methanesulfonamide starting material.

EXAMPLE 2

Using an identical crude methanesulfonamide, the procedure described in Example 1 was repeated using anhydrous sodium carbonate (0.385 g.) in place of the potassium carbonate. As in Example 1, gas evolution was observed upon addition of the base; however, the amount of gas was judged to be less than that observed in Example 1. Analysis of the dried methanesulfonamide product derived from this treatment indicated an $NH_4^+$ concentration of 500 ppm, as compared to 1750 ppm in the crude methanesulfonamide starting material.

EXAMPLE 3

Using an identical crude methanesulfonamide, the procedure described in Example 1 was repeated using anhydrous potassium pyrophosphate (1.200 g.) in place of the potassium carbonate. In contrast to Examples 1 and 2, no obvious gas evolution was observed upon addition of the base. Analysis of the dried methanesulfonamide product from this treatment indicated an $NH_4^+$ concentration of 770 ppm, as compared to 1750 ppm in the crude methanesulfonamide starting material.

EXAMPLE 4

Using an identical crude methanesulfonamide, the procedure described in Example 1 was repeated using sodium pyrophosphate decahydrate (1.620 g.) in place of the potassium carbonate. As in Example 3, no obvious gas evolution was observed upon addition of the base. Analysis of the methanesulfonamide product from this treatment, after THF stripping and overnight drying, indicated an $NH_4^+$ concentration of 270 ppm, as compared to 1750 ppm in the crude methanesulfonamide starting material.

EXAMPLE 5

Preparation of the base Potassium Methanesulfonamide

Methanesulfonamide (20.00 g.) and potassium hydroxide flakes (86.8% KOH, 13.59 g.) were combined and heated to 90° C. under reduced pressure (60 mmHg), whereupon the methanesulfonamide melted. On further heating to 100° C., the slow evolution of water vapor was observed. The resulting mixture was heated to 145° C. over 2 hours while sparging with $N_2$ and maintaining the 60 mmHg pressure. During this time, the composition of the mixture changed from that of a slurry of suspended KOH in molten methanesulfonamide to that of a brittle white solid. The pressure of the reactor was then reduced to 40 mmHg and the solid heated and held at 145° C. for 1 hour to effect removal of the last traces of water. After cooling to room temperature, the white solid was pulverized to afford the potassium methanesulfonamide product as a white hygroscopic powder (mp 216° C.). Titrimetric analysis of this product revealed a total basicity of 7.6 mEq/g as compared to a theoretical value of 7.5 mEq/g.

The potassium methanesulfonamide, formed as described above, was used as an anhydrous alkali-metal base in the process of this invention, as follows:

Crude methanesulfonamide (19.952 g.) containing 1.08% ammonium methanesulfonate and 0.53% ammonium chloride in tetrahydrofuran (60 g.) was charged to a stirred glass reactor fitted to a distillation head/receiver and an $N_2$ inlet line positioned to sweep the head space of the reactor. The vent from the distillation head was fitted with a bubbler containing phenolphthalein indicator solution. Solid potassium methanesulfonamide (0.524 g.) as prepared in Example 5 was added to the mixture and the resulting slurry heated to 56° C., whereupon the phenolphthalein indicator in the bubbler turned red, indicating the evolution of $NH_3$ gas from the reaction mixture. Further heating to 63° C. resulted in complete dissolution of the solids in the reaction solvent with the evolution of additional $NH_3$. The tetrahydrofuran solvent was distilled from the mixture, and the resulting liquid heated to 120° C., decanted from the reactor and allowed to cool and solidify. Analysis of the methanesulfonamide product from this treatment revealed an $NH_4^+$ concentration of <5 ppm, as compared to 3500 ppm in the crude methanesulfonamide starting material.

EXAMPLE 6

Using an apparatus similar to that described in Example 5, crude methanesulfonamide (20.015 g.) containing 1.00% ammonium methanesulfonate and 0.51% ammonium chloride was mixed with potassium methanesulfonamide (0.497 g., as prepared in Example 5) in the absence of organic solvent. Upon heating to 95°, the mixture was observed to melt with evolution of $NH_3$ as determined by the color change of the phenolphthalein indicator. The mixture was then further heated to 125° C., held at that temperature for 20 minutes, then decanted and allowed to solidify. Analysis of the methanesulfonamide product from this treatment revealed an $NH_4^+$ concentration of <5 ppm, as compared to 3300 ppm in the crude methanesulfonamide starting material.

EXAMPLE 7

In an apparatus similar to that described in Example 5, tetrahydrofuran (85 g.) and crude methanesulfonamide (15.00 g.), containing 1.11% ammonium methanesulfonate, 0.55% ammonium chloride and 0.52% ammonium methanesulfonide, was charged to the reactor and heated to 53° C. Aqueous NaOH (13%, 1.36 g.) was added resulting in the immediate evolution of $NH_3$ vapor, as evidenced by the color change of the phenolphthalein indicator in the bubbler, and the formation of a small amount of suspended white solid. The mixture was heated to reflux and the solvent taken overhead. As the solvent was removed and the temperature of the mixture was allowed to increase to 88° C., the suspended solid was observed to slowly dissolve in the mixture. Continued heating to 105° C. resulted in removal of essentially all of the solvent and water resulting from the aqueous caustic. The homogeneous liquid residue was decanted and allowed to solidify. While reduced ammonium ion concentration resulted from this experiment, the need for separation and removal of water required for adaptation of this process for commercial use is disadvantageous. It is important that the base used in the process of this invention be anhydrous or substantially anhydrous and that it not generate a substantial amount of water as part of the neutralization procedure. This is of particular importance when the base-treatment is performed in water-miscible solvents, e.g., tetrahydrofuran, since water in the solvent after recovery can impede its recyclability, or require expensive solvent drying procedures.

We claim:

1. A method for the preparation of an alkanesulfonamide containing a reduced amount of ammonium salt impurities comprising the treatment of an alkanesulfonamide containing ammonium or alkylammonium-salt impurities with a base under substantially anhydrous conditions and in an amount sufficient to convert substantially all of the ammonium or alkylammonium salts to the corresponding base salts, and liberating neutral amine or ammonia from the reaction, said base selected from the group consisting of alkali-metal and alkaline-earth metal bases, quaternary ammonium and phosphonium bases, and synthetic polymeric resins containing basic functionalities.

2. The method of claim 1 where the alkanesulfonamide has the general formula:

where R is a $C_1$–$C_{20}$ alkyl group, and $R^1$ and $R^2$ are independently hydrogen or a $C_1$–$C_{20}$ alkyl group.

3. The method of claim 1 wherein said alkanesulfonamide is first formed prior to the base treating step by the method comprising reacting, in a volatile organic solvent, at least 2 molar equivalents of an amine of the formula $R^1R^2NH$, where $R^1$ and $R^2$ are independently hydrogen or a $C_1$–$C_{20}$ alkyl group, with one molar equivalent of an alkanesulfonyl halide of the formula $RSO_2X$, where R is a $C_1$–$C_{20}$ alkyl group and X is fluorine, chlorine, bromine or iodine, the crude product of the reaction substantially containing alkanesulfonamide and ammonium or alkyl-ammonium halide, ammonium or alkylammonium alkanesulfonate, and ammonium or alkylammonium alkanesulfonimide.

4. The method of claim 3 wherein, prior to the base treatment step, said crude product has been treated to remove at least a substantial proportion of the ammonium halide or amine hydrohalide.

5. The method of claim 4 wherein the alkanesulfonamide containing said ammonium or alkylammonium salt impurities is base treated while dissolved in a volatile organic solvent.

6. The method of claim 5 wherein said volatile organic solvent is at least one of acetonitrile, 1,2-dimethoxyethane, diethoxymethane, 1,3-dioxolane, 1,4-dioxane, a $C_1$–$C_4$ nitroalkane, propionitrile, tetrahydrofuran or toluene.

7. The method of claim 4 wherein said base is the alkali-metal or alkaline-earth metal oxide, hydroxide, carbonate, bicarbonate, phosphate, pyrophosphate or pyrophosphate hydrate.

8. The method of claim 4 wherein said base is a $C_4$–$C_{32}$ tetra(alkyl) or tetra(arylalkyl) ammonium or phosphonium hydroxide, carbonate, phosphate or pyrophosphate.

9. The method of claim 4 wherein said base is a synthetic polymeric resin containing hydroxide, carbonate, phosphate or pyrophosphate functional groups.

10. The method of claim 7 wherein said pyrophosphate hydrate is the decahydrate.

11. The method of claim 4 wherein said base is an alkali-metal or alkaline-earth metal alkanesulfonamide.

12. The method of claim 4 wherein the solvent is physically removed from the crude alkanesulfonamide prior to the base treating step.

13. The method of claim 4 wherein said base is an alkanesulfonamide having the formula $(RSO_2NR^1)_xM$ where R is a $C_1$–$C_{20}$ alkyl group, $R^1$ is hydrogen or a $C_1$–$C_{20}$ alkyl group, and M is the alkali-metal or alkaline-earth metal, and x corresponds to the valency of the metal.

14. The method of claim 13 wherein said base is the sodium or potassium alkanesulfonamide.

15. The method of claim 3 for preparing the alkanesulfonamide wherein the volatile organic solvent is tetrahydrofuran and the alkanesulfonyl halide is the alkanesulfonyl chloride.

16. The method of claim 15 wherein the amine of the formula $R^1R^2NH$ represents ammonia and the alkane-sulfonyl chloride is methanesulfonyl chloride.

17. The method of claim 16 wherein the volatile organic solvent of the base treating step is tetrahyrofuran.

18. The method of claim 17 wherein said base is an alkali-metal or alkaline-earth metal oxide, hydroxide, carbonate, bicarbonate, phosphate, pyrophosphate, pyrophosphate-hydrate or alkanesulfonamide.

19. The method of claim 18 wherein said base is an alkali-metal or alkaline-earth metal hydroxide.

20. The method of claim 18 wherein said base is an alkali-metal or alkaline-earth metal carbonate.

21. The method of claim 18 wherein said base is an alkali-metal or alkaline-earth metal pyrophosphate or phosphite.

22. The method of claim 18 wherein said base is an alkali-metal or alkaline-earth metal methanesulfonamide.

23. The method of claim 16 wherein said base is a $C_4$–$C_{32}$ tetra(alkyl) or tetra(arylalkyl) ammonium hydroxide, carbonate, phosphate or pyrophosphate, or the phosphonium analogues thereof.

24. The method of claim 4 wherein the base treating step is carried out by passing the crude product through a packed column or static bed of the base in solid form.

25. The method of claim 16 wherein the base treating step is carried out by passing the filtered crude product through a packed column or static bed of the base in solid form.

26. The method of claim 24 wherein said base is an alkali-metal or alkaline-earth metal phosphate or pyrophosphate.

* * * * *